United States Patent [19]

Trantow et al.

[11] Patent Number: 5,987,991
[45] Date of Patent: Nov. 23, 1999

[54] DETERMINATION OF RAYLEIGH WAVE CRITICAL ANGLE

[75] Inventors: Richard L. Trantow, Cincinnati; Manohar Bashyam, West Chester, both of Ohio

[73] Assignee: General Electric Company, Cincinnati, Ohio

[21] Appl. No.: 09/002,499

[22] Filed: Jan. 2, 1998

[51] Int. Cl.⁶ .......................... G01N 29/10; G01N 29/26
[52] U.S. Cl. ................................ 73/624; 73/625; 73/628; 73/634
[58] Field of Search .......................... 73/597, 599, 602, 73/620, 621, 622, 624, 625, 627, 628, 632, 633, 634

[56] References Cited

U.S. PATENT DOCUMENTS

| | | | |
|---|---|---|---|
| 2,799,157 | 7/1957 | Pohlman | 73/624 |
| 2,819,613 | 1/1958 | Neiley | 73/627 |
| 2,995,925 | 8/1961 | Worlton | 73/627 |
| 3,340,953 | 9/1967 | Zemanek, Jr. | 367/28 |
| 3,512,400 | 5/1970 | Lynnworth | 73/597 |
| 3,580,057 | 5/1971 | Seegmiller | 73/597 |
| 3,937,067 | 2/1976 | Flambard et al. | 73/627 |
| 4,098,129 | 7/1978 | Deblaere et al. | 73/599 |
| 4,210,028 | 7/1980 | Hildebrand | 73/598 |
| 4,338,820 | 7/1982 | Jassby et al. | 73/597 |
| 4,435,985 | 3/1984 | Wickramasinghe | 73/642 |
| 4,462,256 | 7/1984 | Moffett | 73/642 |
| 4,524,621 | 6/1985 | Yamanaka | 73/597 |
| 4,574,637 | 3/1986 | Adler et al. | 73/629 |
| 4,606,235 | 8/1986 | Kindt | 74/113 |
| 4,674,334 | 6/1987 | Chimenti et al. | 73/627 |
| 4,765,196 | 8/1988 | Russ | 74/436 |
| 4,817,016 | 3/1989 | Thompson et al. | 364/507 |
| 5,024,093 | 6/1991 | Sasaki et al. | 73/633 |
| 5,079,952 | 1/1992 | Nakaso et al. | 73/624 |
| 5,111,696 | 5/1992 | Lund et al. | 73/627 |
| 5,402,681 | 4/1995 | Nakaso et al. | 73/602 |
| 5,481,945 | 1/1996 | Whipple et al. | 74/820 |

OTHER PUBLICATIONS

"Measurement of Applied and Residual Stresses Using an Ultrasonic Instrumentation System", by B.E. Gordon, Jr., ISA Transactions, vol. 19, No. 2, pp. 33–41.

"Acoustic Evaluation Of Cold Work In 316 Stainless Steel Tubing And Plate", R.L. Trantow, Prepared for the U.S. Atomic Energy Commission Division of Reactor Development and Technology, Jun., 1973.

Primary Examiner—Hezron Williams
Assistant Examiner—Rose M. Miller
Attorney, Agent, or Firm—Andrew C. Hess; Gerry S. Gressel

[57] ABSTRACT

A method of non-destructively evaluating or validating a processed area of an object such as a metallic laser shock peened surface by determining Rayleigh wave angles at various positions on the surface. The Rayleigh wave angle is determined by: (a) directing incident beams of ultrasonic waves onto at least one point of a surface at a plurality of incident angles; (b) simultaneously measuring intensity of a combination of corresponding directly reflected and re-radiated beams at a plurality of corresponding reflected angles equal in magnitude to the incident angles with respect to a line normal to the surface; (c) generating a null angle profile of data indicating intensity versus corresponding incident angles from measured intensities in step (b); (d) determining an intensity curve by applying a polynomial curve fit to a low intensity portion of the null angle profile; and (e) determining the effective critical angle for the corresponding Rayleigh wave by determining a substantially minimum point on the curve. The polynomial curve fit may be a second order polynomial fit and the plurality of incident angles and corresponding reflected angles are predetermined and in close proximity to a predetermined critical angle.

17 Claims, 4 Drawing Sheets

DETERMINATION OF RAYLEIGH WAVE CRITICAL ANGLE

BACKGROUND OF THE INVENTION

This patent is related to U.S. application Ser. No. 09/002,355, filed Jan. 2, 1998, still pending.

FIELD OF THE INVENTION

The present invention generally relates to the non-destructive testing of material using ultrasonic waves and, in particular, a method for non-destructive validation of laser shock peened metallic materials or measuring the magnitude of the laser shock effect using Rayleigh wave or Stonely wave critical angles.

DISCUSSION OF THE BACKGROUND ART

Laser shock peening or laser shock processing, as it also referred to, is a process for producing a region of deep compressive residual stresses imparted by laser shock peening a surface area of a workpiece. Laser shock peening typically uses multiple radiation pulses from high power pulsed lasers to produce shock waves on the surface of a workpiece similar to methods disclosed in U.S. Pat. No. 3,850,698, entitled "Altering Material Properties"; U.S. Pat. No. 4,401,477, entitled "Laser Shock Processing"; and U.S. Pat. No. 5,131,957, entitled "Material Properties". Laser peening as understood in the art and as used herein utilizes a laser beam to produce a strong localized compressive force on a portion of a surface by producing an explosive force. The explosive force is produced by instantaneous ablation or vaporization of a painted or coated or uncoated surface beneath a force containing overlay which is typically a water curtain. Laser peening has been utilized to create a compressively stressed protection layer at the outer surface of a workpiece which is known to considerably increase the resistance of the workpiece to fatigue failure as disclosed in U.S. Pat. No. 4,937,421, entitled "Laser Peening System and Method". Many methods and uses for using laser shock peening have been developed and could benefit from an accurate method of validation and non-destructive testing of effects of the process. Known methods include directing a beam of ultrasonic waves on to the surface of the material at a variable angle of incidence, detecting the energy of the corresponding reflected beam, and determining the critical angle of incidence at which the energy (or the amplitude of the reflected waves) appear to pass through a minimum. At the critical angle the acoustic energy within the material propagates along the surface of the material in what are defined as Rayleigh or Stonely waves which decrease logarithmically in amplitude with depth. Together with couplant velocities and Snell's Law, the critical angle can be used to calculate the propagation speed of the Rayleigh ultrasonic waves at the surface of the material. It is well known that these surface waves are useful in comparing material properties and changes in these properties.

An article in the ISA Transactions, Vol. 19, No. 2, published in 1980, entitled "Measurement of Applied and Residual Stresses" discloses an ultrasonic instrumentation system developed for nondestructive measurements of applied and residual stresses. The article discloses a system that measures time of flight of an ultrasonic wave through a material with a resolution of 0.1 nanoseconds and discusses how time of flight correlates directly with elastic stress levels. U.S. Pat. No. 4,210,028, entitled "Method And Apparatus For Ultrasonically Measuring Concentrations Of Stress", discloses an apparatus and method for ultrasonically measuring concentrations of stress in objects of interest. The apparatus includes an ultrasonic transducer array for propagating acoustic waves in the object along a plurality of determinable directions and from a plurality of determinable positions. Time of flight measurements are made and reconstructed into a map of the variations in acoustic velocity within the object. The changes in acoustic velocity are then mathematically converted into a map of stress concentration areas in the object of interest.

It is believed that laser shock peening imparts increased resistance to crack initiation and propagation resulting from cyclic fatigue by producing compressive residual stresses in the laser shock peened material. In addition to the compressive residual stress, the material may also be strengthened by the local work hardening due to plastic deformation at the site of the laser shock. Also, the orientation and degree of preferential crystallographic texture are expected to affect the fatigue damage tolerance of the part. All of these structural conditions affect the velocity of the different modes of acoustic wave propagation within a material. The wave propagation mode employed in this methodology is referred to as a Rayleigh wave, or Stonely wave. These are surface waves that decrease exponentially in amplitude with depth into the material. The velocity sensing methodology described in this disclosure employs Rayleigh waves generated by refraction, and senses their presence by a decrease, or "null" in the amplitude of the ultrasonic beam that is both reflected and re-radiated from the part's surface. It is well recognized that the Rayleigh or critical angle at the null may be used to determine and analyze absolute and relative material properties for evaluation and comparative purposes.

The Rayleigh wave may be generated by refraction of the incident acoustic beam at a liquid solid interface where the liquid, often water, is referred to as a couplant. The angle at which an incident longitudinal or compressional wave is refracted and converted to a Rayleigh wave propagating parallel with the surface of the material is referred to as the Rayleigh Critical Angle. Changes in the Rayleigh Critical Angle at which these surface waves are generated are an indicator of changes in the Rayleigh wave velocity and, therefore, an indicator of changes in material properties.

It has been found that the angle at which the Rayleigh Wave is generated is evidenced by a "sharp" decrease, or "null" in the intensity profile of the superimposed reflected and re-radiated acoustic beam. The depth of the null has been found to be a function of the attenuation within the material and of the wave length or frequency of the acoustic beam. There is a frequency related maximum null condition, and there is also a phase change associated with the received signal that is dependent on whether the frequency of the incident beam is above or below that associated with the maximum null. Because of these effects, simply measuring the changes in the amplitude of the received signal at some single fixed angle slightly smaller or larger than the Rayleigh Critical Angle (on the slope of the null) will result in indications colored by the effects of many material properties such as grain size, preferential crystallographic orientation or texture, work hardening, etc. and measurement related variables such as couplant temperature. To separate the effects of attenuation from properties related to residual stress and texture some means of directly determining the angular position of the null must be employed in a quick and effective manner suitable for process validation in a production environment. The prior art methods for determining critical angles are very time consuming and a more practical method for process evaluation and product validation is highly desirable. The present invention is directed towards this purpose. The present method provides a non-destructive material evaluation technique using ultrasonic waves and the determination of effective Rayleigh wave critical angles for use in quality control to evaluate the degree of change in properties due to materials processing operations such as laser shock peening. The effective Rayleigh wave critical angles of the present invention may not be exact but are sufficient for use in quality control to evaluate the degree of change in properties due to materials processing operations.

SUMMARY OF THE INVENTION

The present invention provides a method for determining effective Rayleigh wave critical angles at a surface of an object and particularly of a metallic object and in a more particular embodiment for a laser shock peened surface of a metallic object. The method is particularly useful if there is a predetermined critical angle such as may be the case for non-destructive validation of laser shock peened metallic materials. The present invention provides a method for determining effective Rayleigh wave critical angles at a surface of a metallic object, including the following steps: (a) directing incident beams of ultrasonic waves onto at least one point of the surface at a plurality of incident angles; (b) simultaneously measuring intensity of a combination of corresponding directly reflected and re-radiated beams at a plurality of corresponding reflected angles equal in magnitude to the incident angles with respect to a line normal to the surface; (c) generating a null angle profile of data indicating intensity versus corresponding incident angles from measured intensities in step (b); (d) determining an intensity curve by applying a curve fit, such as a polynomial curve fit, to a mid to lower intensity portion of the null angle profile; and (e) determining the effective critical angle for the corresponding Rayleigh waves, the effective critical angle being equal to a determined angle of incidence at which the energy of the reflected beam is substantially a minimum point on the curve. The polynomial curve fit may be a second order polynomial fit and the plurality of incident angles and corresponding reflected angles may be predetermined and in close proximity to a predetermined critical angle.

The present invention also provides a method for mapping effective Rayleigh wave critical angles on a surface area of an object. This method includes: (a) scanning incident beams of ultrasonic waves along the area at a plurality of incident angles; (b) simultaneously measuring intensity of a combination of corresponding directly reflected and re-radiated beams at a plurality of corresponding reflected angles equal in magnitude to the incident angles with respect to a line normal to the surface; (c) generating a plurality of null angle profiles of data indicating intensity versus corresponding incident angles from measured intensities in step (b) at a plurality of points (data acquisition locations) on the area; (d) determining intensity curves for the points by applying a polynomial curve fits to mid to lower intensity portions of the null angle profiles for each data acquisition location on the surface; and (e) determining the effective critical angles for the corresponding Rayleigh waves, the effective critical angles being equal to determined angles of incidence at which the energy of the reflected beams are substantially minimum points on the respective curves. The scanning preferably includes a plurality of passes of continuous movement of the pitch and catch transducers such that during each pass the incident and reflected angles respectively are held constant. The pitch and catch transducers may be operated in bursts or alternatively continuously over the points in the area during each pass. The passes may include intermittent movement of the pitch and catch transducers wherein during each pass the incident and reflected angles respectively are held constant and the pitch and catch transducers are operated at intermittent stops at points along the area.

ADVANTAGES

The present invention has many advantages over similar methods in the prior art and, in particular, it offers a faster more accurate method of directing a beam of ultrasonic waves on to the surface of the material at a variable angle of incidence, detecting the energy of the corresponding reflected beam, and determining an effective critical angle of incidence at which the energy (or the amplitude of the reflected waves) passes through a minimum. The method of the present invention is also advantageous because it reduces inaccuracy due to effects of many other material properties such as grain size, preferential crystallographic orientation or texture, work hardening, etc. and measurement related variables such as couplant temperature.

Yet another advantage of the present invention is that it has consistent results and is reproducible and, therefore, highly suitable for process validation in a production environment.

These features and advantages will become more readily apparent in the following description when taken in conjunction with the appended drawings.

BRIEF DESCRIPTION OF THE DRAWINGS

The invention, together with further objects and advantages thereof, is more particularly described in conjunction with the accompanying drawings in which.

DETAILED DESCRIPTION

Figure 1:
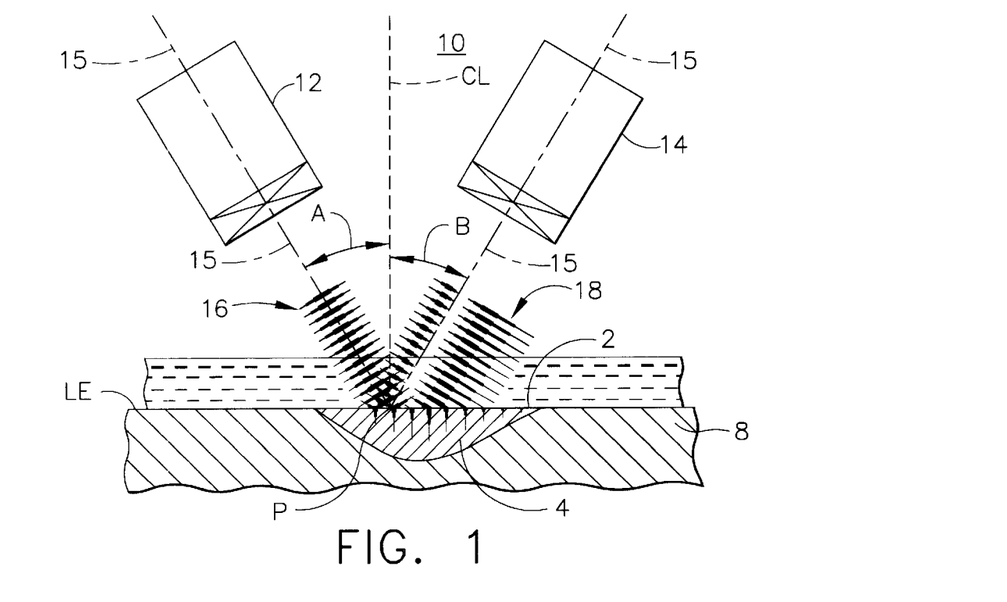
FIG. 1 is a general diagram of a dual angle goniometer used in an exemplary method of the present invention.
Figure 2:
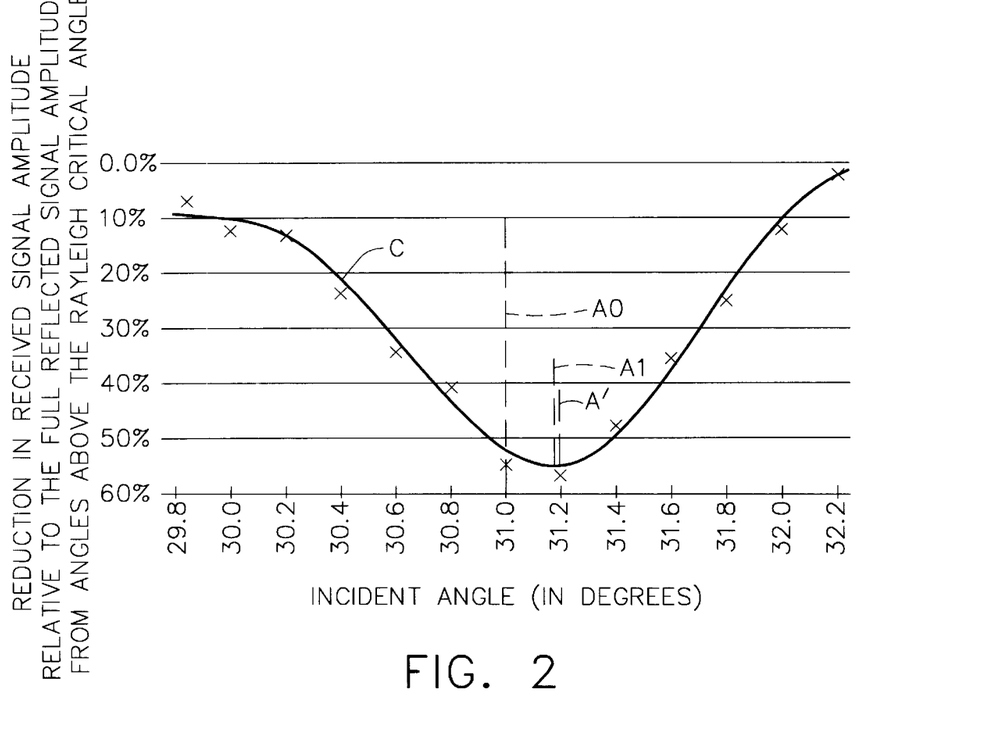
FIG. 2 is a diagram illustrating fitting a polynomial to a low amplitude portion of data representing an intensity versus incident angle profile in accordance with the present invention.
Figure 3:
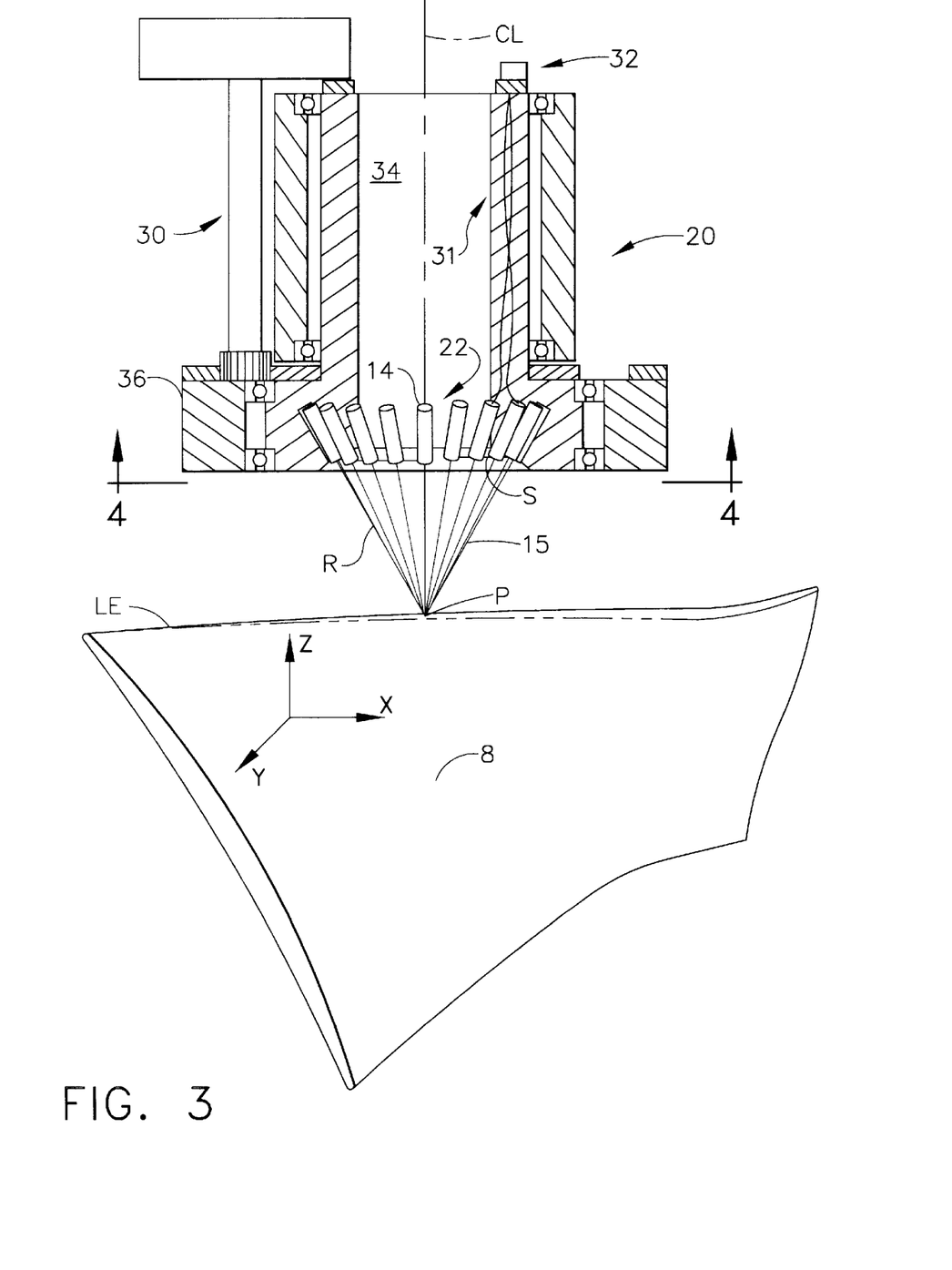
FIG. 3 is a partial perspective and partial cut away illustration of an alternative scanning apparatus using a plurality of fixed angle ultrasonic transducers for use with a method of the present invention.
Figure 4:
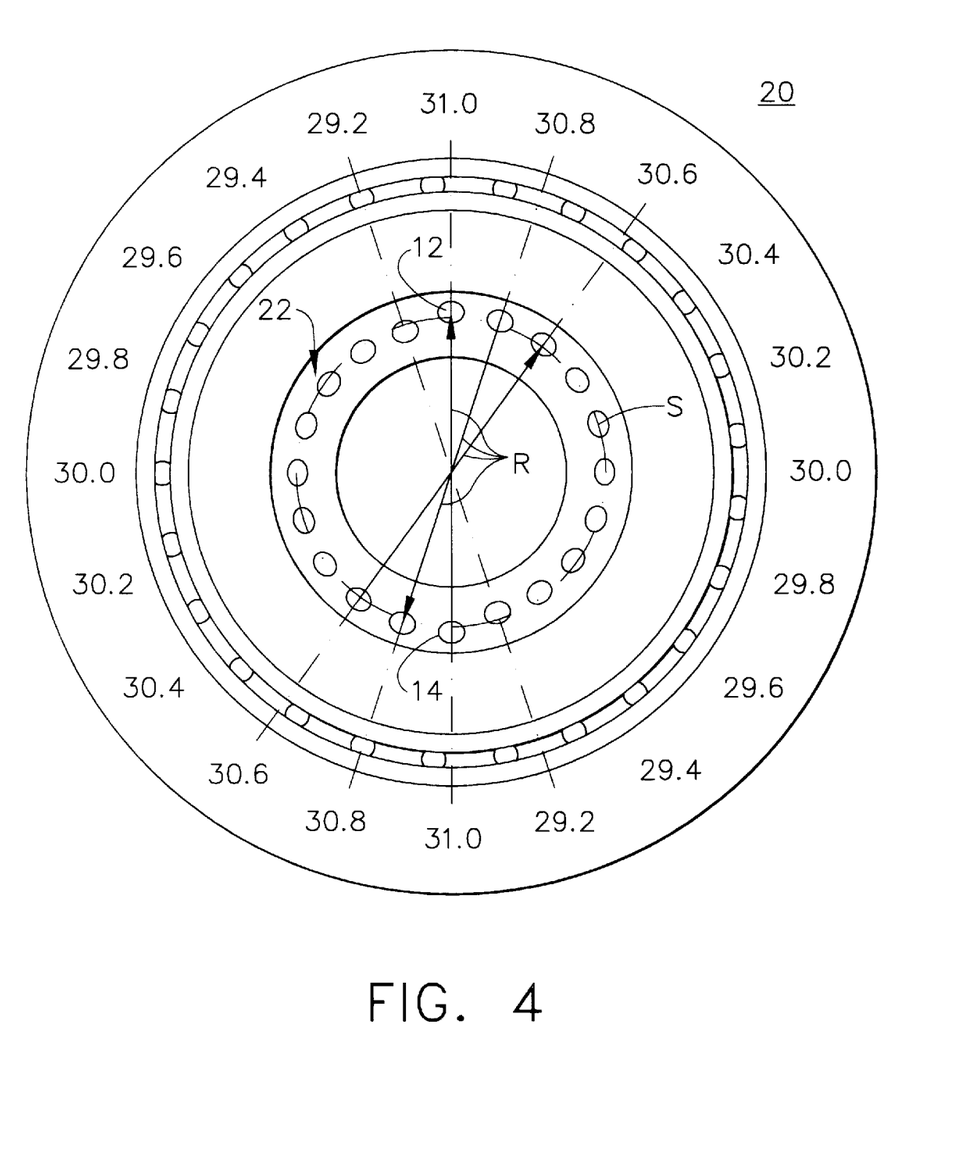
FIG. 4 is an elevated illustrative view through 4—4 of the rotatable transducer array and fixture in FIG. 3.

Referring now to the drawings, there is schematically illustrated in FIG. 1 a portion of an ultrasonic scanning apparatus 10 (such as a conventional dual angle goniometer or the scanning apparatus illustrated shown in FIGS. 3 and 4) showing an adjustable pair of pitch and catch ultrasonic transducers 12 and 14, respectively, positioned to interrogate a laser shock peened surface 2 of a laser shock peened region 4 of an object, particularly a hard metallic object such as a leading edge LE of a fan blade 8 (shown in FIG. 3). The pitch and catch ultrasonic transducers 12 and 14 are positioned to simultaneously transmit towards and receive from the laser shock peened surface 2 incident and reflective ultrasonic waves 16 and 18, respectively. The pitch and catch ultrasonic transducers 12 and 14 are angularly aligned at incident and reflective angles A and B respectively which are equal in magnitude about a centerline CL of the ultrasonic scanning apparatus 10 which is also held normal to the laser shock peened surface 2 at the point P which is to be interrogated. The transducers are positioned to transmit and/or receive the incident and reflective ultrasonic waves 16 and 18, respectively, along axes of transmission 15 at the same point P on the centerline CL which is to be held normal to the laser shock peened surface 2 at the point P. The incident and reflective angles A and B respectively are typically measured between the axes of transmission 15 and the centerline CL. Not shown, but well known in the art of goniometers and ultrasonic scanning apparatuses, are angle adjustment means to equi-angularly adjust the angular alignment of the transducers 12 and 14 at equal incident and reflective angles A and B at the point P. It is well known in the art to adjust pitch and catch transducers 12 and 14, respectively, to determine an actual critical angle A', as illustrated in FIG. 2, at a point P of a metal surface.

To both speed the angular adjustment, and minimize operator variability and error, one embodiment of this critical angle measurement methodology employs either a series of fixed mechanically defined positional stops and/or a series of programmed positional stops at which critical angle signal amplitude measurements could be automatically made and recorded e.g. the intensity data points X at 0.2 degree intervals about the predetermined critical angle A0 which is illustrated as 31 degrees in FIG. 2. These programmed stops could be based on the sensing of a series of angularly related features on the transducer positioning mechanism, or on some form of a positional encoder either directly or indirectly related to the transducer positioning structure.

Figure 5:
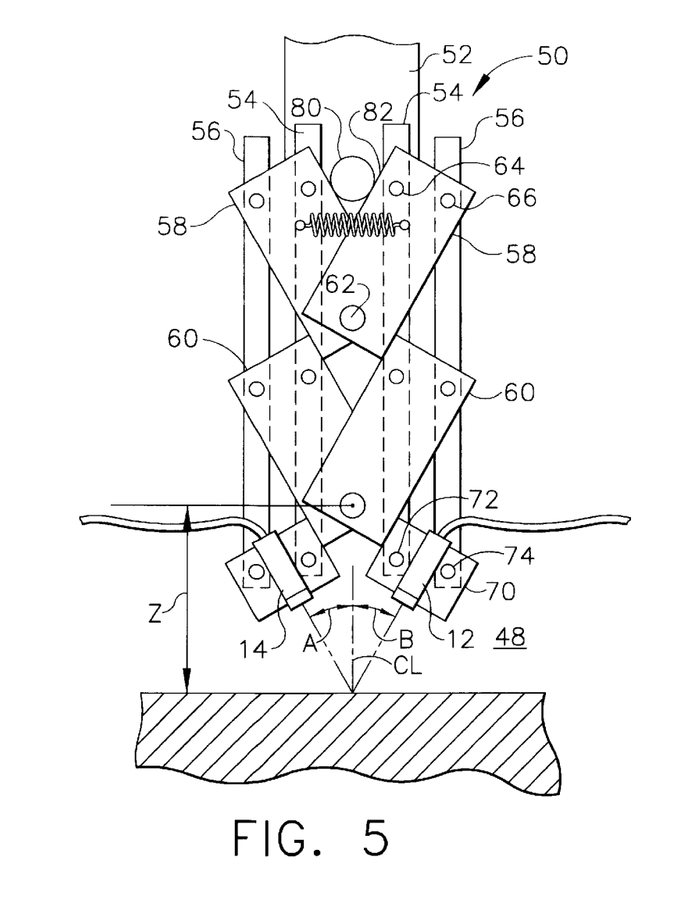
FIG. 5 is an elevated view illustration of a part of another alternative scanning apparatus using a pair angle ultrasonic transducers for use with a method of the present invention.
Figure 6:
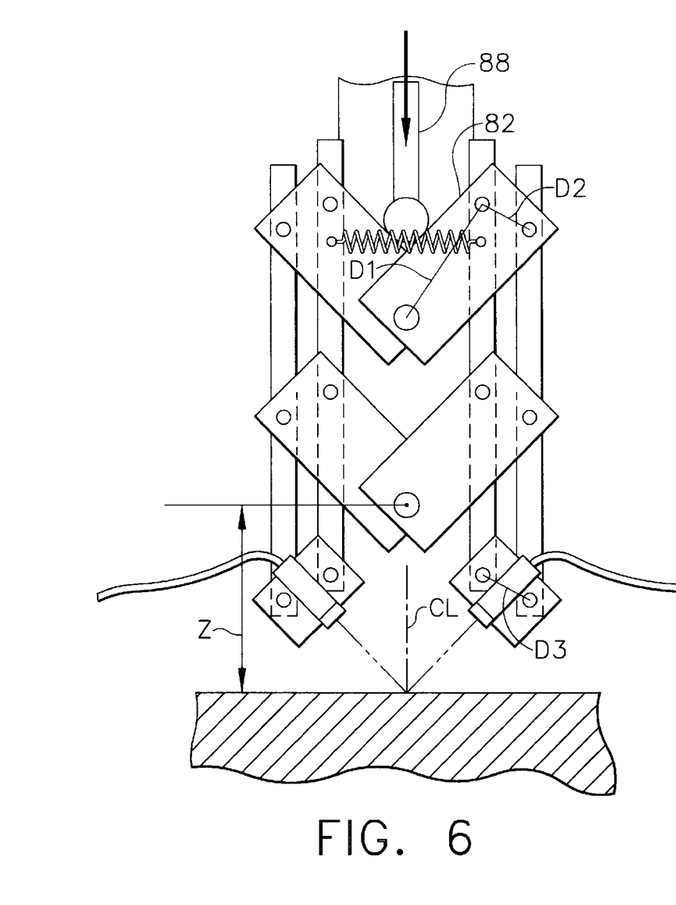
FIG. 6 is an elevated view illustration of the apparatus of the scanning apparatus in FIG. 5 using a the pair angle ultrasonic transducers at a different incident angle.

An embodiment of such a two transducer system 48 is shown in FIGS. 5 and 6 and provides the invention with two modes of operation. A first mode is to perform either full line or full area scans of the surface of interest at each of the stops defined or pre-programmed incident angles of interest. A second mode steps through the angles of interest at each point along the line or at each point within the area of interest before moving on to the next data point. This dual transducer system employs a linkage 50 that allows the transducers to be angled through various incident and reflective angles A and B respectively and still have the axes of transmission 15 maintain the same intersection at the same point P along the centerline CL which is to be held normal to the laser shock peened surface 2 at the point P at the surface of the material being evaluated. The intersection at point P serves as a virtual pivot point for the transducer's beam axes 15, thus enabling the use of the system in the evaluation of larger surface areas that would otherwise interfere with the real pivot points associated with conventional goniometer assemblies.

The linkage 50 includes right and left hand first, second, and third bars 52, 54 and 56 respectively which are held parallel to the centerline 15 of the transducer system 48. The first, second, and third bars 52, 54 and 56 respectively are linked together by right and left hand spaced apart first and second plates 58 and 60 respectively at first, second, and third pivot points 62, 64 and 66 respectively so that any movement of the bars results in parallel displacement of the bars from each other and the centerline CL. In order to accomplish this, first lines of action indicated by first distances D1 between the first and second pivot points 62 and 64 respectively along the first and second plates 58 and 60 respectively are equal and second lines of action indicated by second distances D2 between the second and third pivot points 64 and 66 respectively along the first and second plates 58 and 60 respectively are equal. The first lines of action are always parallel to each other and the second lines of action are always parallel to each other. A third plate 70 is pivotally connected to the second and third bars 54 and 56 respectively at fourth and fifth pivot points 72 and 74 respectively and has a third line of action indicated by third distance D3 between the fourth and fifth pivot points that is equal to and parallel to the second distances D2. Each of the transducers 12 or 14 is mounted to one of the third plates 70 such that the axes of transmission 15 are always parallel to the first lines of action along the first distances D1. Consequently, the transducers may be set so that their respective axes of transmission 15 are perpendicularly equidistant from the fourth and fifth pivot points.

The incident and reflective angles A and B are adjusted in accordance with the first and second modes above by axial motion of positioning pins 80 (one pin may be sufficient) that act as cam drivers and are driven simultaneously between cam surfaces 82 on the edges of the first plates 58 causing first plates to pivot about the first pivot points 62. A spring 84 is operably disposed between left and right hand first plates 58 to force the edges or cam surfaces 82 of the first plates against the pin 80. The pin 80 is mounted to a controlled drive mechanism 88 (such as a ball screw mechanism) such that the pin may be translated along the centerline CL causing the left and right handed first plates to increase and decrease the angles between them and set the incident and reflective angles A and B accordingly. Note that the incident and reflective angles A and B are linearly related to the translational position of the pin. This capability greatly simplifies the angular positioning and readout by allowing the use of commonly available positioning and readout mechanisms. The two transducer system 48 could be rotated to measure velocities in other directions across the materials surface.

The present invention is a faster more cost effective method of determining and using an effective critical angle A1 to determine processed material properties for process validation. The ultrasonic scanning method of the present invention is particularly useful for validation in a production environment for maintaining quality control of a laser shock peening process where mapping of changes in materials' properties and conditions is of the essence. The incident and reflective angles A and B at which the surface is scanned are preferably predetermined and ultrasonic beam transmission and reception are simultaneously done at small predetermined intervals such as 0.2 degrees about a predetermined critical angle A0 which is illustrated as 31 degrees in FIG. 2. The received signals are converted to an intensity value and may be expressed as a % in reduction of maximum intensity as illustrated in FIG. 2 where these intensity values are profiled as a function of incidence angle at the various starting, stopping, and interval incident angles. A null angle profile 11 of intensity data is illustrated as intensity data points X in FIG. 2.

Next, a preferably second order polynomial curve fit is applied to the profile 11 of intensity data X at a mid to lower or a low amplitude portion of the profile, such as between about the 20% to 60% range of the data, as illustrated by curve C in FIG. 2. The profile 11 is preferably stored in a computer for which standardized mathematical routines are available to determine a curve fit and/or a polynomial equation using methods such as a least square fit of the data. The profile 11 of intensity data X and the polynomial curve C may both be displayed on a monitor in a manner similar to that in FIG. 2. An effective critical angle A1 which is relatively close to the actual critical angle A' may be observed from the curve C or be determined by mathematical means preferably using a polynomial equation derived from the polynomial curve fit at the minimum along the curve C. The effective critical angle A1 along the laser shock peened area of the surface may be mapped for use in quality control and as a means for non-destructive testing. Note that it is important to hold the centerline normal to the surface at the point P which is to be interrogated or ultrasonically scanned.

It has been found that 10 to 15 different angles of incidence provide a good number of intensity data points X for determining the second order polynomial equation using the least squares fit of the data to the second order polynomial. This could result in a very time consuming and potentially error prone process if the angles had to be adjusted at a great many points on a large area to be mapped for critical angles, such as a laser shock peened leading edge LE of a gas turbine engine fan blade as illustrated in FIG. 3. This drawback is addressed by another embodiment of the present invention, which scans an area of interest, for example the laser shock peened leading edge, one incremental angle at a time. The entire area is scanned at each of the predetermined incident and reflective angles A and B respectively near the predetermined critical angle A0. Alternatively the transducer head may be rotated at each successive data acquisition point on the material surface so as to bring all transducer pairs of interest to the desired rotational orientation (relative to the part or scan direction) for acquisition before completing the move to the next successive data acquisition point. The fixed predetermined incident and reflective angles A and B respectively are incrementally changed and fixed for the next scan. This procedure is repeated for each incremental set of predetermined incident and reflective angles such that the entire area is scanned at each predetermined incremental incidence angle until the entire area has been scanned in this manner for all the predetermined incident and reflective angles A and B. The ultrasonic transmitting transducers may use pulse tone burst or continuous signal excitation at each incident angle, while simultaneously effecting movement between the transducers and the area being scanned. Alternatively, the scanning process may stop intermittently at each point P on the surface area. The polynomial curve fit is applied to determine the effective critical angle at the point P as described above. In this manner the effective critical angle may be mapped for the entire laser shock peened surface or area of interest.

Another variation on this method is to pulse the ultrasonic transducers as the area is scanned while simultaneously effecting continuous movement between the transducers and the area being scanned. The scanning pitch and receive transducers may be moved at a constant velocity with respect to the area being mapped while the transmitting transducer is pulsed at a constant rate, and each pass of the transducers at an incrementally different incident angle can be coordinated such that the same points P in the area are interrogated on each pass. If this cannot be accomplished accurately enough then interpolation on the surface coordinates of the area such as x and y can be used to assign intensity values for each incident angle at predetermined points P on the surface in the area of interest in order to assemble the intensity vs. incident angle profile of the present invention.

This area wide ultrasonic scanning method for critical angle mapping may be accomplished using a rotatable scanning head 20 illustrated in FIGS. 3–5 in which a rotatable array 22 of pitch and catch transducer pairs (12 and 14 in FIG. 1) are held in place and which can be translated in a x, y, and z orthogonal co-ordinate system and positioned substantially normal to the surface at point P. The pitch and catch ultrasonic transducers 12 and 14 respectively, in each pair, are oppositely disposed about and equally angled with respect to a centerline of the array, and all the transducers are positioned to transmit and/or receive the incident and reflective ultrasonic waves 16 and 18, respectively, at the same point on the centerline which is to be held normal to the laser shock peened surface 2 at the point P. Each pair of the opposing transducers are fixed in the rotatable scanning head 20 during the scanning and preferably located along a dual spiral S where the spirals are mirror images on either side of the rotatable scanning head. The spirals are along a fixed radius R spherical surface whose center of curvature coincides with the center P1 of the incident beams footprint on the surface under examination which of course coincides with the point P. Each pair of transducers are fixed at a slightly different incident angle relative to the surface normal, and are rotated into position for data acquisition along a specific direction on the surface. The direction along the surface can be along the x, y, and z coordinates.

Additional pairs of transducers, used to interrogate the reflected beam intensity at angles outside the high resolution angular interrogation range, may also be incorporated in this dual spiral array. These special pairs of transducers may be used to provide total reflection beam reference amplitudes. This configuration provides that if all transducers have the same effective diameter then they will have the same beam maximum (Y0) location from the face of the transducer, and hence the same beam footprint diameter and intensity at the surface under evaluation. If multiple frequency interrogation of the surface is to be conducted, the radius R of the transducer's spherical locating surface, the transducer's diameter, and the transducers primary resonant frequency, should be selected to position the beams location at the surface under evaluation at the highest tone burst frequency to be used (potentially a harmonic of the primary resonant frequency). All lower frequency beams will thus intersect the surface in their more spatially uniform far field regions.

For those cases where the angular change in null location is known to be small about the predetermined and effective critical angles, the angular coverage provided by these transducers may not need to be continuous. This is because, for data processing based null detection schemes, the angular location of the beam null is primarily determined by a polynomial (or similar function) fit of the beam intensity slopes on either side of the null rather than on the null itself. It is noted that if the level of attenuation (due primarily to grain size within the material) is desired, acquisition of the effective returning beam amplitude at the null should be provided (i.e., continuous angular coverage across the null region becomes necessary).

One feature of this configuration is that the characteristics of the null or intensity profile used to determine the effective critical angle at a given point P on the surface under examination can be generated with a single rotation of the transducer and rotatable scanning head. A single rotation of the rotatable transducer head could be used to bring every incrementally angled pair of fixed incident angle transducers in the array to any number of angular orientations with respect to the surface, limited only by the directional resolution required and the time considerations of the examination. This assumes some form of angular positional feedback means to send signals to and from the rotation head to control the orientation of the transducers for data acquisition.

FIG. 3 illustrates the rotatable scanning head 20 using a Geneva Drive 30 to rotate it about the centerline CL. The rotatable scanning head 20 includes an angular positional feedback means 30 which would have signal transmission means for coupling of the transmitted and received signals from the transducers and transmitting them out of the rotatable scanning head 20 such as through slip rings 32. The feedback means 30 is preferably also used for activating and controlling the transducers. Other types of signal transmission means may also be used such as rotary transformers, rotary capacitors, and/or optical data link couplers, all well known in the field. The rotatable transducer scanning head and slip ring assembly illustrated herein has a hollow center 34 for visual access to the common beam impingement point P on the surface. This allows optical access to the center P1 of the incident beams footprint on the surface under examination to align the beams from the transducers such that they all impinge on the same point P on the surface and to allow some means of measuring the angular tilt error in the rotary axis or centerline CL of the system relative to the surface normal and to adjust or correct such an angular misalignment.

As the Geneva Drive rotates at a constant angular velocity, the angular velocity of the rotatable transducer head 20 cycles from zero at the data acquisition positions (which are mechanically fixed by the geometry of the drive) to a maximum at the mid point between acquisitions. At high rotational rates, these cyclic variations in angular velocity can cause considerable vibration if inertial unbalancing effects are not countered. One inertial balancing means which may be used to counter these is a counter-rotating annular collar 36 encircling the rotary transducer head. The collar has an angular inertia roughly equal to that of the rotating transducer head about their common axis of rotation which is the centerline. The collar is preferably driven by the Geneva Drive that rotates the transducer head, or it may be indirectly driven from the rotating transducer head through an idler gear (not shown). In either case, as the transducer head accelerates in one direction the inertial balancing collar accelerates in the opposite direction, thus balancing the reaction and minimizing vibration.

In the simplest (and least efficient) form of this system, each pair of transducers could be activated individually if necessitated by excessive crosstalk between receiving transducers (particularly between adjacent receiving transducers). However, simultaneous interrogation of all directional angles, provided by the rotational position of the transducers around the rotary head, is the operational mode of choice in minimizing the data acquisition time. In the event chat crosstalk is not a problem, all transmitting transducers 12 may be ganged together and driven simultaneously, preferably by a tone burst. Tone burst excitation is preferred as a more stable steady state acoustic beam may be generated by the transducer at frequencies below (or in harmonic multiples above) its primary resonant frequency. A full rotation of the transducer head is still required to measure all incident angles in all directions, i.e. different transducer pair angular orientations around the centerline CL. In the event that cross talk between adjacent receivers is a problem of limited proportion, the propagation directions could be alternated as seen in the graphic (i.e., transmitter-receiver-transmitter-receiver, etc. around the ring). The number of transmitting transducers ganged together could be limited to smaller more orthogonally oriented groups to further limit sensitivity to cross talk.

In all cases, signals from the receiving transducers are treated individually, with their own (under most circumstances gated) signal (peak, peak to peak, or RMS) level detection and logging circuitry. The resultant basic data output of this system and method is expected to be a series of files containing returning signal amplitude for each excitation frequency, from each incident angle transducer pair, at each desired surface wave propagation direction, and at each pixel location on the surface under examination as explained above. From these data, The Rayleigh Critical Angle and level of returning signal amplitude may be determined as a basis for the generation of maps of the various acoustic characteristics of the surfaces under examination (i.e. velocity and attenuation with respect to frequency). For instance plots of velocity with respect to direction at a specific point on the surface for evaluation of anisotropic characteristics, or plots of velocity with respect to frequency for evaluation of depth effects. In the case of LSP, these plots are expected to be the primary measure of LSP based residual stress effects in a material.

The foregoing descriptive embodiments of the invention have been presented for the purpose of describing and illustrating the invention. It is not intended to be exhaustive or to limit the invention to the precise form disclosed and obviously many modifications and variations are possible in light of the above teachings. While the preferred embodiment of the invention has been described fully in order to explain its principles, it is understood that various modifications or alterations may be made to the preferred embodiment without departing from the scope of the invention as set forth in the appended claims.

What is claimed is:

1. A method for determining Rayleigh wave effective critical angles at a surface of an object, said method comprising the steps of:
   (a) directing incident beams of ultrasonic waves onto at least one point of the surface at a plurality of incident angles;
   (b) simultaneously measuring intensity of a combination of corresponding directly reflected and re-radiated beams at a plurality of corresponding reflected angles equal in magnitude to said incident angles with respect to a line normal to the surface;
   (c) generating a null angle profile of data indicating intensity versus corresponding incident angles from measured intensities in step (b);
   (d) determining an intensity curve by applying a polynomial curve fit to a low intensity portion of the null angle profile; and
   (e) determining the effective critical angle by determining a substantially minimum point on the curve, said effective critical angle being equal to a determined angle of incidence at which the energy of the reflected beam is the substantially minimum point on the curve.

2. A method as claimed in claim 1 wherein said polynomial curve fit is a second order polynomial fit.

3. A method as claimed in claim 1 wherein the plurality of incident angles and corresponding reflected angles are predetermined and in close proximity to a predetermined angle.

4. A method as claimed in claim 3 wherein said polynomial curve fit is a second order polynomial fit.

5. A method as claimed in claim 3 wherein said object is metallic and said surface is a laser shock peened surface.

6. A method for mapping Rayleigh wave effective critical angles on a surface area of an object, said method comprising the steps of:
   (a) scanning incident beams of ultrasonic waves at a plurality of points on the area at a plurality of incident angles;

(b) simultaneously measuring intensity of a combination of corresponding directly reflected and re-radiated beams at a plurality of corresponding reflected angles equal in magnitude to said incident angles with respect to a line normal to the surface;

(c) generating a plurality of null angle profiles of data indicating intensity versus corresponding incident angles from measured intensities in step (b) at the plurality of points on the area;

(d) determining intensity curves for said points by applying a polynomial curve fits to low intensity portions of the null angle profiles at their respective points on the surface; and (e) determining the effective critical angles by determining substantially minimum points on the curves, said effective critical angles being equal to determined angles of incidence at which the energy of the reflected beams are the substantially minimum points on the respective curves.

7. A method as claimed in claim 6 wherein said polynomial curve fits are second order polynomial fits.

8. A method as claimed in claim 6 wherein the plurality of incident angles and corresponding reflected angles are predetermined and in close proximity to at least one predetermined angle.

9. A method as claimed in claim 8 wherein said polynomial curve fits are second order polynomial fits.

10. A method as claimed in claim 8 wherein said object is metallic and said surface is a laser shock peened surface.

11. A method as claimed in claim 6 wherein the scanning comprises a plurality of passes of continuous movement of the pitch and catch transducers wherein during each pass the incident and reflected angles respectively are held constant.

12. A method as claimed in claim 11 wherein the pitch and catch transducers are operated in bursts over the points in the area during each pass.

13. A method as claimed in claim 11 wherein the pitch and catch transducers are operated continuously during each pass over the area.

14. A method as claimed in claim 11 wherein the scanning comprises a plurality of passes with intermittent movement of the pitch and catch transducers wherein during each pass the incident and reflected angles respectively are held constant and the pitch and catch transducers are operated at intermittent stops at the points along the area.

15. An apparatus for ultrasonic scanning of a surface, said apparatus comprising:

a pair of 180 degree oppositely disposed ultrasonic right and left side transducers having beam axes;

a positioning means for positioning said transducers such that said beam axes intersect a centerline at a single point and said beam axes are equiangular with respect to said centerline;

said positioning means having right and left side first, second, and third bars; and right and left side spaced apart first and second plates link together said right and left side first, second, and third bars at first, second, and third pivot points respectively such that movement of said bars results in parallel displacement of said bars from each other and said centerline.

16. An apparatus as claimed in claim 15 further comprising:

said right and left side transducers mounted on right and left side third plates pivotally connected to said right and left side second and third bars at fourth and fifth pivot points respectively such that said axes of transmission are always pivotal about a single virtual pivoting point on said centerline.

17. An apparatus as claimed in claim 16 further comprising:

first lines of action having first distances between said first and second pivot points along said first and second plates;

second lines of action having second distances between said second and third pivot points along said first and second plates;

said first distances are equal to each other and said second distances are equal to each other;

said first lines of action are held always parallel to each other and said second lines of action are held always parallel to each other;

right and left side third plates are pivotally connected to said right and left side second and third bars respectively at fourth and fifth pivot points and have third lines of action having third distances between said right and left side fourth and fifth pivot points respectively; and said third lines of action are parallel to said second lines of action and said third distances are equal to said second distances.

* * * * *